United States Patent
Ludwig et al.

(10) Patent No.: US 9,981,009 B2
(45) Date of Patent: May 29, 2018

(54) SOLUBLE FCγ RECEPTOR FOR TREATMENT OF AUTOIMMUNE BULLOUS DISEASES

(71) Applicant: SuppreMol GmbH, Martinsried/Munich (DE)

(72) Inventors: Ralf Ludwig, Luebeck (DE); Peter Sondermann, Stockdorf (DE); Dominik Ter Meer, Munich (DE)

(73) Assignee: SUPPREMOL GMBH, Martinsreid/Munich (DE)

( * ) Notice: Subject to any disclaimer, the term of this patent is extended or adjusted under 35 U.S.C. 154(b) by 0 days. days.

(21) Appl. No.: 15/029,994

(22) PCT Filed: Oct. 16, 2013

(86) PCT No.: PCT/EP2013/071599
§ 371 (c)(1),
(2) Date: Apr. 15, 2016

(87) PCT Pub. No.: WO2015/055240
PCT Pub. Date: Apr. 23, 2015

(65) Prior Publication Data
US 2016/0235814 A1    Aug. 18, 2016

(51) Int. Cl.
*A61K 38/16* (2006.01)
*A61K 38/17* (2006.01)
*C07K 14/735* (2006.01)
*A61K 9/00* (2006.01)
*A61K 45/06* (2006.01)

(52) U.S. Cl.
CPC ........ *A61K 38/1774* (2013.01); *A61K 9/0019* (2013.01); *A61K 45/06* (2013.01); *C07K 14/70535* (2013.01)

(58) Field of Classification Search
CPC .................... A61K 38/1774; A61K 9/0019
See application file for complete search history.

(56) References Cited

U.S. PATENT DOCUMENTS

| 7,655,229 B2 | 2/2010 | Chan et al. |
| 2009/0053218 A1 | 2/2009 | Koenig et al. |

FOREIGN PATENT DOCUMENTS

| EP | 1006183 A1 | 6/2000 |
| EP | 2161031 A1 | 3/2010 |
| JP | 2005-515981 A | 6/2005 |
| JP | 2016-503289 A | 2/2016 |
| WO | 2015/055240 A1 | 4/2015 |

OTHER PUBLICATIONS

Ludwig et al (2013), Dermatology, vol. 89, No. 5, pp. 915-925.*
International Search Report for International Application No. PCT/EP2013/071599 filed Oct. 16, 2013.
Kasperkiewicz et al., Genetic identification and functional validation of FcgammaRIV as key molecule in autoantibody-induced tissue injury. Journal of Pathology, 228:8-19 (2012).

* cited by examiner

*Primary Examiner* — Prema Mertz
(74) *Attorney, Agent, or Firm* — K&L Gates LLP; Louis C. Cullman; Hal Gibson

(57) ABSTRACT

The invention generally relates to the field of biotechnology and medicine. It provides an agent, a pharmaceutical composition and a kit for treatment of autoimmune bullous diseases (AMDB). More specifically, the invention relates to the use of a soluble Fc gamma receptor for treating AMDB, and a pharmaceutical composition and a kit comprising said receptor. It further involves a method of treatment of AMDB.

10 Claims, 5 Drawing Sheets

SEQUENCE LISTING

<160> NUMBER OF SEQ ID NOS: 12

<210> SEQ ID NO 1
<211> LENGTH: 177

<212> TYPE: PRT
<213> ORGANISM: artificial
<220> FEATURE:
<223> OTHER INFORMATION: soluble Fc gamma receptor IIB

<400> SEQUENCE: 1

| Met | Ala | Pro | Pro | Lys | Ala | Val | Leu | Lys | Leu | Glu | Pro | Gln | Trp | Ile | Asn |
| 1 | | | | 5 | | | | | 10 | | | | | 15 | |

| Val | Leu | Gln | Glu | Asp | Ser | Val | Thr | Leu | Thr | Cys | Arg | Gly | Thr | His | Ser |
| | | | 20 | | | | | 25 | | | | | 30 | | |

| Pro | Glu | Ser | Asp | Ser | Ile | Gln | Trp | Phe | His | Asn | Gly | Asn | Leu | Ile | Pro |
| | | | 35 | | | | | 40 | | | | | 45 | | |

| Thr | His | Thr | Gln | Pro | Ser | Tyr | Arg | Phe | Lys | Ala | Asn | Asn | Asn | Asp | Ser |
| | | 50 | | | | | 55 | | | | | 60 | | | |

| Gly | Glu | Tyr | Thr | Cys | Gln | Thr | Gly | Gln | Thr | Ser | Leu | Ser | Asp | Pro | Val |
| 65 | | | | | 70 | | | | | 75 | | | | | 80 |

| His | Leu | Thr | Val | Leu | Ser | Glu | Trp | Leu | Val | Leu | Gln | Thr | Pro | His | Leu |
| | | | | 85 | | | | | 90 | | | | | 95 | |

| Glu | Phe | Gln | Glu | Gly | Glu | Thr | Ile | Val | Leu | Arg | Cys | His | Ser | Trp | Lys |
| | | | | 100 | | | | | 105 | | | | | 110 | |

| Asp | Lys | Pro | Leu | Val | Lys | Val | Thr | Phe | Phe | Gln | Asn | Gly | Lys | Ser | Lys |
| | | | 115 | | | | | 120 | | | | | 125 | | |

| Lys | Phe | Ser | Arg | Ser | Asp | Pro | Asn | Phe | Ser | Ile | Pro | Gln | Ala | Asn | His |
| | 130 | | | | | 135 | | | | | 140 | | | | |

| Ser | His | Ser | Gly | Asp | Tyr | His | Cys | Thr | Gly | Asn | Ile | Gly | Tyr | Thr | Leu |
| 145 | | | | | 150 | | | | | 155 | | | | | 160 |

| Tyr | Ser | Ser | Lys | Pro | Val | Thr | Ile | Thr | Val | Gln | Ala | Pro | Ser | Ser | Ser |
| | | | | 165 | | | | | 170 | | | | | 175 | |

Pro

<210> SEQ ID NO 2
<211> LENGTH: 534
<212> TYPE: DNA
<213> ORGANISM: artificial
<220> FEATURE:
<223> OTHER INFORMATION: soluble Fc gamma receptor IIB

<400> SEQUENCE: 2

| atggcaccgc cgaaagcagt tctgaaactg gaaccgcagt ggattaacgt tctgcaggaa | 60 |
| gatagcgtta ccctgacctg tcgtggcacc catagcccgg aaagcgatag cattcagtgg | 120 |
| tttcacaacg gcaatctgat tccgacccat acccagccga gctatcgttt taaagcgaac | 180 |
| aacaacgata gcggcgaata tacctgtcag accggtcaga ccagcctgag cgatccggtt | 240 |
| catctgaccg ttctgagcga atggctggtt ctgcagaccc cgcatctgga atttcaggaa | 300 |
| ggcgaaacca ttgttctgcg ttgccacagc tggaaagata aaccgctggt taaagttacc | 360 |
| ttcttccaga acggcaaaag caaaaaattc agccgtagcg atccgaattt tagcattccg | 420 |
| caggcgaatc atagccatag cggcgattat cattgtaccg gcaacattgg ctataccctg | 480 |
| tatagcagca aaccggtgac cattaccgtt caggcgccga gcagcagccc gtaa | 534 |

<210> SEQ ID NO 3
<211> LENGTH: 181
<212> TYPE: PRT
<213> ORGANISM: human
<220> FEATURE:
<221> NAME/KEY: misc_feature
<222> LOCATION: (1)..(181)
<223> OTHER INFORMATION: human Fc gamma RIIB

<400> SEQUENCE: 3

```
Met Gly Thr Pro Ala Ala Pro Pro Lys Ala Val Leu Lys Leu Glu Pro
1               5                   10                  15
Gln Trp Ile Asn Val Leu Gln Glu Asp Ser Val Thr Leu Thr Cys Arg
            20                  25                  30
Gly Thr His Ser Pro Glu Ser Asp Ser Ile Gln Trp Phe His Asn Gly
        35                  40                  45
Asn Leu Ile Pro Thr His Thr Gln Pro Ser Tyr Arg Phe Lys Ala Asn
    50                  55                  60
Asn Asn Asp Ser Gly Glu Tyr Thr Cys Gln Thr Gly Gln Thr Ser Leu
65                  70                  75                  80
Ser Asp Pro Val His Leu Thr Val Leu Ser Glu Trp Leu Val Leu Gln
                85                  90                  95
Thr Pro His Leu Glu Phe Gln Glu Gly Glu Thr Ile Val Leu Arg Cys
            100                 105                 110
His Ser Trp Lys Asp Lys Pro Leu Val Lys Val Thr Phe Phe Gln Asn
        115                 120                 125
Gly Lys Ser Lys Lys Phe Ser Arg Ser Asp Pro Asn Phe Ser Ile Pro
    130                 135                 140
Gln Ala Asn His Ser His Ser Gly Asp Tyr His Cys Thr Gly Asn Ile
145                 150                 155                 160
Gly Tyr Thr Leu Tyr Ser Ser Lys Pro Val Thr Ile Thr Val Gln Ala
                165                 170                 175
Pro Ser Ser Ser Pro
            180
```

<210> SEQ ID NO 4
<211> LENGTH: 543
<212> TYPE: DNA
<213> ORGANISM: human
<220> FEATURE:
<221> NAME/KEY: misc_feature
<222> LOCATION: (1)..(5443)
<223> OTHER INFORMATION: human Fc gamma RIIB

<400> SEQUENCE: 4

```
atggggacac ctgcagctcc cccaaaggct gtgctgaaac tcgagcccca gtggatcaac    60
gtgctccagg aggactctgt gactctgaca tgccggggga ctcacagccc tgagagcgac   120
tccattcagt ggttccacaa tgggaatctc attcccaccc acacgcagcc cagctacagg   180
ttcaaggcca acaacaatga cagcggggag tacacgtgcc agactggcca gaccagcctc   240
agcgaccctg tgcatctgac tgtgctttct gagtggctgg tgctccagac ccctcacctg   300
gagttccagg agggagaaac catcgtgctg aggtgccaca gctggaagga caagcctctg   360
gtcaaggtca cattcttcca gaatggaaaa tccaagaaat ttccccgttc ggatcccaac   420
ttctccatcc cacaagcaaa ccacagtcac agtggtgatt accactgcac aggaaacata   480
ggctacacgc tgtactcatc caagcctgtg accatcactg tccaagctcc cagctcttca   540
ccg                                                                 543
```

<210> SEQ ID NO 5
<211> LENGTH: 184
<212> TYPE: PRT
<213> ORGANISM: human
<220> FEATURE:
<221> NAME/KEY: misc_feature
<222> LOCATION: (1)..(184)

<223> OTHER INFORMATION: human Fc gamma RIIA

<400> SEQUENCE: 5

| Met | Gly | Thr | Pro | Ala | Ala | Pro | Pro | Lys | Ala | Val | Leu | Lys | Leu | Glu | Pro |
|---|---|---|---|---|---|---|---|---|---|---|---|---|---|---|---|
| 1 | | | | 5 | | | | | 10 | | | | | 15 | |

| Pro | Trp | Ile | Asn | Val | Leu | Gln | Glu | Asp | Ser | Val | Thr | Leu | Thr | Cys | Gln |
|---|---|---|---|---|---|---|---|---|---|---|---|---|---|---|---|
| | | | 20 | | | | | 25 | | | | | 30 | | |

| Gly | Ala | Arg | Ser | Pro | Glu | Ser | Asp | Ser | Ile | Gln | Trp | Phe | His | Asn | Gly |
|---|---|---|---|---|---|---|---|---|---|---|---|---|---|---|---|
| | | 35 | | | | | 40 | | | | | 45 | | | |

| Asn | Leu | Ile | Pro | Thr | His | Thr | Gln | Pro | Ser | Tyr | Arg | Phe | Lys | Ala | Asn |
|---|---|---|---|---|---|---|---|---|---|---|---|---|---|---|---|
| 50 | | | | | 55 | | | | | 60 | | | | | |

| Asn | Asn | Asp | Ser | Gly | Glu | Tyr | Thr | Cys | Gln | Thr | Gly | Gln | Thr | Ser | Leu |
|---|---|---|---|---|---|---|---|---|---|---|---|---|---|---|---|
| 65 | | | | | 70 | | | | | 75 | | | | | 80 |

| Ser | Asp | Pro | Val | His | Leu | Thr | Val | Leu | Ser | Glu | Trp | Leu | Val | Leu | Gln |
|---|---|---|---|---|---|---|---|---|---|---|---|---|---|---|---|
| | | | | 85 | | | | | 90 | | | | | 95 | |

| Thr | Pro | His | Leu | Glu | Phe | Gln | Glu | Gly | Glu | Thr | Ile | Met | Leu | Arg | Cys |
|---|---|---|---|---|---|---|---|---|---|---|---|---|---|---|---|
| | | | 100 | | | | | 105 | | | | | 110 | | |

| His | Ser | Trp | Lys | Asp | Lys | Pro | Leu | Val | Lys | Val | Thr | Phe | Phe | Gln | Asn |
|---|---|---|---|---|---|---|---|---|---|---|---|---|---|---|---|
| | | 115 | | | | | 120 | | | | | 125 | | | |

| Gly | Lys | Ser | Gln | Lys | Phe | Ser | His | Leu | Asp | Pro | Thr | Phe | Ser | Ile | Pro |
|---|---|---|---|---|---|---|---|---|---|---|---|---|---|---|---|
| 130 | | | | | 135 | | | | | 140 | | | | | |

| Gln | Ala | Asn | His | Ser | His | Ser | Gly | Asp | Tyr | His | Cys | Thr | Gly | Asn | Ile |
|---|---|---|---|---|---|---|---|---|---|---|---|---|---|---|---|
| 145 | | | | | 150 | | | | | 155 | | | | | 160 |

| Gly | Tyr | Thr | Leu | Phe | Ser | Ser | Lys | Pro | Val | Thr | Ile | Thr | Val | Gln | Val |
|---|---|---|---|---|---|---|---|---|---|---|---|---|---|---|---|
| | | | | 165 | | | | | 170 | | | | | 175 | |

| Pro | Ser | Met | Gly | Ser | Ser | Pro |
|---|---|---|---|---|---|---|
| | | | 180 | | | |

<210> SEQ ID NO 6
<211> LENGTH: 554
<212> TYPE: DNA
<213> ORGANISM: human
<220> FEATURE:
<221> NAME/KEY: misc_feature
<222> LOCATION: (1)..(554)
<223> OTHER INFORMATION: human Fc gamma RIIA

<400> SEQUENCE: 6

```
atggggacac ctgcagctcc cccaaaggct gtgctgaaac ttgagccccc gtggatcaac    60
gtgctccagg aggactctgt gactctgaca tgccaggggg ctcgcagccc tgagagcgac   120
tccattcagt ggttccacaa tgggaatctc attccaccc acacgcagcc cagctacagg   180
ttcaaggcca acaacaatga cagcggggag tacacgtgcc agactggcca gaccagcctc   240
agcgaccctg tgcatctgac tgtgctttcc gaatggctgg tgctccagac ccctcacctg   300
gagttccagg agggagaaac catcatgctg aggtgccaca gctggaagga caagcctctg   360
gtcaaggtca cattcttcca gaatggaaaa tcccagaaat tctcccattt ggatcccacc   420
ttctccatcc cacaagcaaa ccacagtcac agtggtgatt accactgcac aggaaacata   480
ggctacacgc tgttctcatc caagcctgtg accatcactg tccaagtgcc cagcatgggc   540
agctcttcac caat                                                    554
```

<210> SEQ ID NO 7
<211> LENGTH: 182
<212> TYPE: PRT
<213> ORGANISM: human
<220> FEATURE:
<221> NAME/KEY: misc_feature

```
<222> LOCATION: (1)..(182)
<223> OTHER INFORMATION: human Fc gamma RIIIA

<400> SEQUENCE: 7

Met Asp Leu Pro Lys Ala Val Val Phe Leu Glu Pro Gln Trp Tyr Arg
1               5                   10                  15

Val Leu Glu Lys Asp Ser Val Thr Leu Lys Cys Gln Gly Ala Tyr Ser
            20                  25                  30

Pro Glu Asp Asn Ser Thr Gln Trp Phe His Asn Glu Ser Leu Ile Ser
        35                  40                  45

Ser Gln Ala Ser Ser Tyr Phe Ile Asp Ala Ala Thr Val Asp Asp Ser
    50                  55                  60

Gly Glu Tyr Arg Cys Gln Thr Asn Leu Ser Thr Leu Ser Asp Pro Val
65                  70                  75                  80

Gln Leu Glu Val His Ile Gly Trp Leu Leu Leu Gln Ala Pro Arg Trp
                85                  90                  95

Val Phe Lys Glu Glu Asp Pro Ile His Leu Arg Cys His Ser Trp Lys
            100                 105                 110

Asn Thr Ala Leu His Lys Val Thr Tyr Leu Gln Asn Gly Lys Gly Arg
        115                 120                 125

Lys Tyr Phe His His Asn Ser Asp Phe Tyr Ile Pro Lys Ala Thr Leu
    130                 135                 140

Lys Asp Ser Gly Ser Tyr Phe Cys Arg Gly Leu Val Gly Ser Lys Asn
145                 150                 155                 160

Val Ser Ser Glu Thr Val Asn Ile Thr Ile Thr Gln Gly Leu Ser Val
                165                 170                 175

Ser Thr Ile Ser Ser Phe
            180

<210> SEQ ID NO 8
<211> LENGTH: 546
<212> TYPE: DNA
<213> ORGANISM: human
<220> FEATURE:
<221> NAME/KEY: human
<222> LOCATION: (1)..(546)
<223> OTHER INFORMATION: human Fc gamma RIIIA

<400> SEQUENCE: 8
atggatctcc caaaggctgt ggtgttcctg gagcctcaat ggtacagggt gctcgagaag      60
gacagtgtga ctctgaagtg ccagggagcc tactcccctg aggacaattc cacacagtgg     120
tttcacaatg agagcctcat ctcaagccag gcctcgagct acttcattga cgctgccaca     180
gttgacgaca gtggagagta caggtgccag acaaacctct ccaccctcag tgacccggtg     240
cagctagaag tccatatcgg ctggctgttg ctccaggccc ctcggtgggt gttcaaggag     300
gaagacccta ttcacctgag gtgtcacagc tggaagaaca ctgctctgca taaggtcaca     360
tatttacaga atggcaaagg caggaagtat tttcatcata attctgactt ctacattcca     420
aaagccacac tcaaagacag cggctcctac ttctgcaggg ggcttgttgg gagtaaaaat     480
gtgtcttcag agactgtgaa catcaccatc actcaaggtt tgtcagtgtc aaccatctca     540
tcattc                                                                546

<210> SEQ ID NO 9
<211> LENGTH: 182
<212> TYPE: PRT
<213> ORGANISM: human
<220> FEATURE:
```

<220> FEATURE:
<221> NAME/KEY: misc_feature
<222> LOCATION: (1)..(182)
<223> OTHER INFORMATION: human Fc gamma RIIIB

<400> SEQUENCE: 9

```
Met Asp Leu Pro Lys Ala Val Val Phe Leu Glu Pro Gln Trp Tyr Ser
1               5                   10                  15
Val Leu Glu Lys Asp Ser Val Thr Leu Lys Cys Gln Gly Ala Tyr Ser
            20                  25                  30
Pro Glu Asp Asn Ser Thr Gln Trp Phe His Asn Glu Asn Leu Ile Ser
        35                  40                  45
Ser Gln Ala Ser Ser Tyr Phe Ile Asp Ala Ala Thr Val Asn Asp Ser
    50                  55                  60
Gly Glu Tyr Arg Cys Gln Thr Asn Leu Ser Thr Leu Ser Asp Pro Val
65                  70                  75                  80
Gln Leu Glu Val His Ile Gly Trp Leu Leu Leu Gln Ala Pro Arg Trp
                85                  90                  95
Val Phe Lys Glu Glu Asp Pro Ile His Leu Arg Cys His Ser Trp Lys
            100                 105                 110
Asn Thr Ala Leu His Lys Val Thr Tyr Leu Gln Asn Gly Lys Asp Arg
        115                 120                 125
Lys Tyr Phe His His Asn Ser Asp Phe His Ile Pro Lys Ala Thr Leu
    130                 135                 140
Lys Asp Ser Gly Ser Tyr Phe Cys Arg Gly Leu Val Gly Ser Lys Asn
145                 150                 155                 160
Val Ser Ser Glu Thr Val Asn Ile Thr Ile Thr Gln Gly Leu Ala Val
                165                 170                 175
Ser Thr Ile Ser Ser Phe
            180
```

<210> SEQ ID NO 10
<211> LENGTH: 486
<212> TYPE: DNA
<213> ORGANISM: human
<220> FEATURE:
<221> NAME/KEY: misc_feature
<222> LOCATION: (1)..(486)
<223> OTHER INFORMATION: human Fc gamma RIIIB

<400> SEQUENCE: 10

```
gacagtgtga ctctgaagtg ccagggagcc tactcccctg aggacaattc cacacagtgg      60
tttcacaatg agaacctcat ctcaagccag gcctcgagct acttcattga cgctgccaca     120
gtcaacgaca gtggagagta caggtgccag acaaacctct ccaccctcag tgacccggtg     180
cagctagaag tccatatcgg ctggctgttg ctccaggccc ctcggtgggt gttcaaggag     240
gaagacccta ttcacctgag gtgtcacagc tggaagaaca ctgctctgca taaggtcaca     300
tatttacaga atggcaaaga caggaagtat tttcatcata attctgactt ccacattcca     360
aaagccacac tcaaagatag cggctcctac ttctgcaggg ggcttgttgg gagtaaaaat     420
gtgtcttcag agactgtgaa catcaccatc actcaaggtt tggcagtgtc aaccatctca     480
tcattc                                                                486
```

<210> SEQ ID NO 11
<211> LENGTH: 176
<212> TYPE: PRT
<213> ORGANISM: artificial
<220> FEATURE:
<223> OTHER INFORMATION: soluble Fc gamma receptor IIB

```
<400> SEQUENCE: 11

Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro Ser Ser Ser Pro
                165                 170                 175

<210> SEQ ID NO 12
<211> LENGTH: 531
<212> TYPE: DNA
<213> ORGANISM: artificial
<220> FEATURE:
<223> OTHER INFORMATION: soluble Fc gamma receptor IIB

<400> SEQUENCE: 12
gcaccgccga aagcagttct gaaactggaa ccgcagtgga ttaacgttct gcaggaagat     60
agcgttaccc tgacctgtcg tggcacccat agcccgaaa gcgatagcat tcagtggttt    120
cacaacggca atctgattcc gacccatacc cagccgagct atcgttttaa agcgaacaac    180
aacgatagcg gcgaatatac ctgtcagacc ggtcagacca gcctgagcga tccggttcat    240
ctgaccgttc tgagcgaatg gctggttctg cagacccgc atctggaatt tcaggaaggc     300
gaaaccattg ttctgcgttg ccacagctgg aaagataaac cgctggttaa agttaccttc    360
ttccagaacg gcaaaagcaa aaaattcagc cgtagcgatc cgaattttag cattccgcag    420
gcgaatcata gccatagcgg cgattatcat tgtaccggca acattggcta taccctgtat    480
agcagcaaac cggtgaccat taccgttcag gcgccgagca gcagcccgta a             531
```

SOLUBLE FCγ RECEPTOR FOR TREATMENT OF AUTOIMMUNE BULLOUS DISEASES

This application is a national phase filing of International Application Number PCT/EP2013/071599 filed on Oct. 16, 2013, the entire disclosure of which is incorporated by reference herein.

FIELD OF THE INVENTION

The invention generally relates to the field of biotechnology and medicine. It provides an agent, a pharmaceutical composition and a kit for treatment of autoimmune bullous diseases (AMDB). More specifically, the invention relates to the use of soluble Fc gamma receptors for treating AMDB, and a pharmaceutical composition and a kit comprising said receptor. It further involves a method of treatment of AMDB.

BACKGROUND

The skin, often referred to as the largest organ of the human body, acts as a waterproof, insulating shield, protecting the body against extremes of temperature, damaging sunlight, harmful chemicals and pathogens. It helps to regulate body temperature and evaporation, and acts as a huge sensor packed with nerves for perceiving and transmitting external stimuli. Skin is made up of two primary layers. The outermost is the epidermis, which consists mainly of highly organized keratinocytes. Complex cellular junctions (desmosomes) connect the keratinocytes to each other, which secrete keratin proteins and lipids forming an extracellular matrix that provides mechanical strength to the skin. The epidermis is bonded to a deeper skin layer below known as the dermis which consists of connective tissue and provides tensile strength and elasticity to the skin through an extracellular matrix composed of collagen fibrils, microfibrils, and elastic fibers, embedded in proteoglycans. Epidermis and dermis are separated by a thin layer called the basement membrane. The dermal-epidermal junction (DEJ) is the area of tissue that joins the epidermal and the dermal layers of the skin.

The autoimmune bullous diseases (AMDB) are a group of skin disorders that primarily affect the skin and mucous membranes. In AMDB, the host immune system disrupts intercellular adhesion molecules or components of the basement membrane in the skin and mucosal surfaces, typically leading to blister formation. Because the intact skin is vital for protecting the body against dehydration and infections, AMDB are often associated with a high degree of morbidity and may be life threatening.

AMDB can be subdivided into four major groups. Intraepidermal blistering diseases (the 'pemphigus group') are characterized by the loss of intercellular connections such as desmosomes, the deposition of immunoreactants at the intercellular junctions of the keratinocytes and the formation of intraepidermal blisters resulting from cell-cell dysadhesion. Typical intraepidermal autoimmune blistering diseases include pemphigus vulgaris (PV) and pemphigus foliaceus (PF). The remainder of the diseases is characterized by subepidermal blister formation resulting from cell-matrix dysadhesion and the deposition of autoantibodies at the dermal-epidermal junction (DEJ). The 'pemphigoid group' includes bullous pemphigoid (BP), mucous membrane pemphigoid (MMP), pemphigoid gestationis, mucous membrane pemphigoid, and linear IgA disease. Lichen planus pemphigoides is sometimes considered a rare variant of BP. The other two groups include epidermolysis bullosa acquisita (EBA), and dermatitis herpetiformis (Mihai and Sitaru, 2007). Bullous systemic lupus erythematosus (BSLE) is a generalized subepidermal blistering disease occurring in patients with systemic lupus erythematosus.

The disruption of structural elements in the skin leading to the typical blister formation in AMDB has been mainly attributed to autoreactive antibodies. Besides, the complement system and autoreactive T cells are thought to be involved in AMDB pathogenesis (Liu and Rubinstein (2008)). Most AMDB are associated with tissue-bound and circulating autoreactive antibodies of the IgG class that typically interact through their Fc portions with factors of the innate immune system, such as the complement system and inflammatory cells, and trigger downstream signaling cascades that ultimately result in tissue destruction (Sitaru et al., 2007). Fc gamma receptors (FcγRs) play a key role in mediating the effector functions of autoreactive IgG antibodies in AMDB.

FcγRs belong to the family of Fc receptors (FcRs) which are crucial for defending the human organism against infections. In general, activating FcγRs and inhibiting FcγRs are to be distinguished. Of the three main FcγRs in humans, FcγRI can bind monomeric IgG, whereas FcγRII and FcγRIII bind to multivalent immune complexes (ICs) composed of antibodies and antigens. (Takai (2002)). Effector functions triggered by FcγRs include, depending on the expressed FcR type and associated proteins, endocytosis with subsequent neutralization of the pathogens and antigen presentation, antibody-dependent cellular cytotoxity (ADCC), secretion of mediators or the regulation of antibody production (Fridman et al. (1992), van de Winkel and Capel (1993)).

One example for the unpredictability of treatment success is Rituximab. The antibody recognizes the CD20-antigen which is exclusively expressed on B cells. After binding to the target Rituximab mediates killing of the B cells with the help of the immune system. Rituximab has been developed for the treatment of B cell lymphoma but since then has been used also for the treatment of autoimmune diseases with an involvement of B cells that are known to produce the pathogenic autoantibodies. A physician familiar with the treatment of autoimmune diseases would certainly consider ITP, SLE or ANCA associated vasculitis as treatable with Rituximab due to their considerable level of autoantibodies. However, treatment success for SLE which is characterized by high levels of autoantibodies could not be demonstrated in two clinical studies (Coca and Sanz (2009)). Similarly, in ANCA associated vasculitis only two third of the patients do respond adequately to Rituximab treatment (Stone (2010)) while in ITP 60% do not respond (Patel (2010)). On the other hand, Rituximab could demonstrate efficacy in multiple sclerosis (Hauser (2008)) and Diabetes type I (Pescowitz (2009)), with both diseases not predominated by considerable levels of autoantibodies To date, conventional AMDB treatment commonly consists of immunosuppressive and anti-inflammatory agents, often at high dosages, and treatment of skin lesions. Unfortunately, many of the drugs used to treat this disease have serious side effects, and patients must be monitored closely for infection, renal and liver function abnormalities, electrolyte disturbances, hypertension, diabetes, anemia, and gastrointestinal bleeding (Mutasim (2007)).

The technical problem underlying the present invention can thus be seen in the provision of an alternative means and method for treating AMDB.

SUMMARY

The present inventors, much to their surprise, found that soluble Fc gamma receptor (sFcγR) reduced disease severity and circulating autoreactive antibodies in an AMDB mouse model in vivo. Further, sFcγR significantly reduced IgG-induced ROS release from neutrophils and impaired dermal epidermal separation—which is thought to play a crucial role cause for the typical blistering—in autoantibody-treated skin grafts. Thus, based on the results provided by the present inventors which are shown in the appended Examples and illustrated in the Figures, sFcγRs hold considerable potential as an agent for treatment of multiple autoimmune bullous diseases.

In view of the utterly complex and distinct events involved in onset and progression of AMDB, and the partly inconsistent effects elicited that are reported in different studies applying sFcγRs treatment of autoimmune diseases, the therapeutic potential of sFcγR for treatment of AMDB could not and was clearly not foreseen. In fact, while sFcγRs treatment was shown in pre-clinical and clinical trials to be beneficial for the treatment of ITP, SLE, MS, it cannot be concluded that treatment of other autoimmune diseases would also be beneficial. Rather, every autoimmune disease has its own peculiarities and each is different, thus, they are not comparable and it cannot be concluded that a successful treatment of one autoimmune disease involving tissue-deposited immune complexes (IC) may also be beneficial for another autoimmune disease involving IC, too. Indeed, involving does not mean that the ICs are the only causative agent of an autoimmune disease, there are many other factors and, thus, no common causative agent of autoimmune disease involving ICs could so far be figured out. In fact, the only common denominator autoimmune diseases, such as those involving ICs, have is that the immune system reacts against body's own structures. A systemic treatment, one could think of for inhibiting the activation of ICs, is to block the Fc receptors of immune cells by way of an antibody as suggested in EP1870422. However, one would not and could not have expected that binding of sFcγRs to the Fc portion of auto-antibodies involved in ICs would result in a beneficial effect for the treatment of AMDB. Without being bound by theory sFcγRs are thought to compete with the membrane FcγRs for the ICs. As a result of the competition the activation of the immune response via the membrane FcγR system is down-modulated. This assumed mode of action would not have been thought to be so effective as seen both in vitro and in the mouse model. Hence, it came as a surprise that sFcγRs work in the treatment of AMDB.

Accordingly, in a first aspect, the present invention relates to a soluble Fc gamma receptor for use in the treatment of autoimmune bullous diseases in a subject. Said subject is preferably a mammal, such as a human, dog, horse, cat, sheep, cattle, cow, rabbit, rat, or mouse, with human being preferred. It is envisaged that the soluble Fc gamma receptor can be used for treatment of multiple blistering diseases, more specifically, the soluble Fc gamma receptor can be used for treatment of, e.g., any of the diseases selected from the group of pemphigus vulgaris (PV), pemphigus foliaceus (PF), bullous pemphigoid (BP), mucous membrane pemphigoid (MMP), pemphigoid gestationis, mucous membrane pemphigoid, linear IgA disease (linear IgA bullous dermatosis), lichen planus pemphigoides, epidermolysis bullosa acquisita (EBA), dermatitis herpetiformis, and bullous systemic lupus erythematosus (BSLE). Although the current inventors have speculated about the use of soluble human FcγRIIB in the treatment of pemphigoid diseases (Clinical Presentation, Pathogenesis, Diagnosis, and Treatment of Epidermolysis Bullosa Acquisita, Ralf J. Ludwig, ISRN Dermatology Volume 2013), it was surprising to find that low concentrations of soluble human FcγRIIB could ameliorate the disease in vivo. The effect of low concentrations of soluble human FcγRIIB are surprising since the person skilled in the art would have suspected that at least an equimolar amount of soluble human FcγRIIB would have to be used to be able to block the binding of pathogenic immune-complexes via Fc part of IgG of ICs would be necessary to stop the auto-antibody driven blister formation in pemphigoid diseases. A second aspect that differentiates the pemphigoid diseases from diseases wherein soluble FcγR has been used is the compartmentalization of the pathogenic reaction, which is strictly localized to the skin tissues. It was neither foreseeable nor known before the present invention, that soluble FcγR was able to elicit any effect in the specialized compartment of the skin. Thus a person skilled in the art might have been inclined to speculate about the use of soluble FcγR in the treatment of auto-immune pemphigoid diseases but the beneficial effect of low concentrations of soluble FcgR on the disease are surprising. Up to now, soluble human FcγRIIB has been successfully used for treating autoimmune diseases where immune complexes are present and occur in the blood, but not in a compartment such as skin. Hence, a skilled person could not have expected the surprising results and the success observed by the present inventors. A third aspect that differentiates the present invention from the review article of Ludwig in ISRN Dermatology Volume 2013 is the fact that the review is not at all clear about the role of FcγRIIB in the etiology of pemphigoid diseases. In particular, the review refers to the publications of Yu et al. (J. Inv. Dermatol. 2010, Vol. 130, No. 12, 2841-2844) who report that FcγRIIA and of FcγRIIIB play a prominent role in destroying tissue in pemphigoid diseases in human. The review also refers to the publication of Kasperkiewicz et al. (J. Pathol. (2012), Vol. 228, No. 1, 8-19) who indicate a prominent role of FcγRIV in destroying tissue in pemphigoid diseases in human. In sum, the review names not less than three FcγRs that play a role in pemphigoid disease and, thus, it could and would not have been expected that the use of soluble FcγRIIB has a beneficial role in treating pemphigoid diseases, since a soluble version of any of the other three FcγRs as referred to in the review could have been a promising tool for combating pemphigoid diseases.

Fc gamma receptors occur in various isoforms. According to the present invention, the soluble Fc gamma receptor can be Fc gamma RIIA, Fc gamma RIIB, Fc gamma RIIIA or Fc gamma RIIIB. However, in one preferred embodiment, the soluble Fc gamma receptor is Fc gamma RIIB.

It is preferred that the soluble Fc gamma receptor is of human origin. It can for example comprise an amino acid sequence selected from the group of SEQ ID No: 1, SEQ ID No: 3, SEQ ID No: 5, SEQ ID No: 7, SEQ ID No: 9, or SEQ ID No: 11. The aforementioned amino acid sequences are encoded by the nucleotide sequences shown in SEQ ID Nos: 2, 4, 6, 8, 10 and 12, respectively. These nucleotide sequences can preferably be used for the production, either synthetically of by way of a vector and host cell system as described herein, of any one of the sFcγRs disclosed herein, in particular those having the amino acid sequence shown in SEQ ID No: 1, SEQ ID No: 3, SEQ ID No: 5, SEQ ID No: 7, SEQ ID No: 9, or SEQ ID No: 11, respectively.

The sequences that the present application refers to are depicted below.

(SM101)
SEQ ID No. 1
MAPPKAVLKL EPQWINVLQE DSVTLTCRGT HSPESDSIQW
FHNGNLIPTH TQPSYRFKAN NNDSGEYTCQ TGQTSLSDPV
HLTVLSEWLV LQTPHLEFQE GETIVLRCHS WKDKPLVKVT
FFQNGKSKKF SRSDPNFSIP QANHSHSGDY HCTGNIGYTL
YSSKPVTITV QAPSSSP

In the amino acid sequence shown in SEQ ID No. 1 the M (methionine) residue at position 1 (i.e., at the start of the amino acid sequence) may lack. This variant amino acid sequence is disclosed herein as SEQ ID No. 11.

(SM101, cDNA)
SEQ ID No. 2
```
  1 ATGGCACCGC CGAAAGCAGT TCTGAAACTG GAACCGCAGT GGATTAACGT TCTGCAGGAA
 61 GATAGCGTTA CCCTGACCTG TCGTGGCACC CATAGCCCGG AAAGCGATAG CATTCAGTGG
121 TTTCACAACG GCAATCTGAT TCCGACCCAT ACCCAGCCGA GCTATCGTTT TAAAGCGAAC
181 AACAACGATA GCGGCGAATA TACCTGTCAG ACCGGTCAGA CCAGCCTGAG CGATCCGGTT
241 CATCTGACCG TTCTGAGCGA ATGGCTGGTT CTGCAGACCC CGCATCTGGA ATTTCAGGAA
301 GGCGAAACCA TTGTTCTGCG TTGCCACAGC TGGAAAGATA AACCGCTGGT TAAAGTTACC
361 TTCTTCCAGA ACGGCAAAAG CAAAAAATTC AGCCGTAGCG ATCCGAATTT TAGCATTCCG
421 CAGGCGAATC ATAGCCATAG CGGCGATTAT CATTGTACCG GCAACATTGG CTATACCCTG
481 TATAGCAGCA AACCGGTGAC CATTACCGTT CAGGCGCCGA GCAGCAGCCC GTAA
```

(human FcγRIIB)
SEQ ID No. 3
MGTPAAPPKA VLKLEPQWIN VLQEDSVTLT CRGTHSPESD SIQWFHNGNL IPTHTQPSYR
FKANNNDSGE YTCQTGQTSL SDPVHLTVLS EWLVLQTPHL EFQEGETIVL RCHSWKDKPL
VKVTFFQNGK SKKFSRSDPN FSIPQANHSH SGDYHCTGNI GYTLYSSKPV TITVQAPSSS
P (human FcγRIIB, cDNA)
SEQ ID No. 4
```
  1 atggggacac ctgcagctcc cccaaaggct gtgctgaaac tcgagcccca gtggatcaac
 61 gtgctccagg aggactctgt gactctgaca tgccggggga ctcacagccc tgagagcgac
121 tccattcagt ggttccacaa tgggaatctc attcccaccc acacgcagcc cagctacagg
181 ttcaaggcca acaacaatga cagcggggag tacgtgcc agactggcca gaccagcctc
241 agcgaccctg tgcatctgac tgtgctttct gagtggctgg tgctccagac ccctcacctg
301 gagttccagg agggagaaac catcgtgctg aggtgccaca gctggaagga caagcctctg
361 gtcaaggtca cattcttcca gaatggaaaa tccaagaaat ttcccgttc ggatcccaac
421 ttctccatcc cacaagcaaa ccacagtcac agtggtgatt accactgcac aggaaacata
481 ggctacacgc tgtactcatc caagcctgtg accatcactg tccaagctcc agctcttca
541 ccg
```

(human FcγRIIA)
SEQ ID No. 5
MGTPAAPPKA VLKLEPPWIN VLQEDSVTLT CQGARSPESD SIQWFHNGNL IPTHTQPSYR
FKANNNDSGE YTCQTGQTSL SDPVHLTVLS EWLVLQTPHL EFQEGETIML RCHSWKDKPL
VKVTFFQNGK SQKFSHLDPT FSIPQANHSH SGDYHCTGNI GYTLFSSKPV TITVQVPSMG
SSSP (human FcγRIIA, cDNA)
SEQ ID No. 6
```
  1 atggggacac ctgcagctcc cccaaaggct gtgctgaaac ttgagccccc gtggatcaac
 61 gtgctccagg aggactctgt gactctgaca tgccaggggg ctcgcagccc tgagagcgac
121 tccattcagt ggttccacaa tgggaatctc attcccaccc acacgcagcc cagctacagg
```

-continued

```
181 ttcaaggcca acaacaatga cagcggggag tacacgtgcc agactggcca gaccagcctc
241 agcgaccctg tgcatctgac tgtgctttcc gaatggctgg tgctccagac ccctcacctg
301 gagttccagg agggagaaac catcatgctg aggtgccaca gctggaagga caagcctctg
361 gtcaaggtca cattcttcca gaatggaaaa tcccagaaat ctcccatttt ggatcccacc
421 ttctccatcc cacaagcaaa ccacagtcac agtggtgatt accactgcac aggaaacata
481 ggctacacgc tgttctcatc aagcctgtg accatcactg tccaagtgcc agcatgggc
541 agctcttcac caat
```

(human FcγRIIIA)                                    SEQ ID No. 7

```
MDLPKAVVFL EPQWYRVLEK DSVTLKCQGA YSPEDNSTQWF HNESLISSQA SSYFIDAATV
DDSGEYRCQ TNLSTLSDPV QLEVHIGWLL LQAPRWVFKEE DPIHLRCHSW KNTALHKVTY
LQNGKGRKY FHHNSDFYIP KATLKDSGSY FCRGLVGSKNV SSETVNITIT QGLSVSTISS
F
```

(human FcγRIIIA, cDNA)                              SEQ ID No. 8

```
  1 atggatctcccaa aggctgtggt gttcctggag cctcaatggt acagggtgct cgagaaggac
 61 agtgtgactc tgaagtgcca gggagcctac tcccctgagg acaattccac acagtggttt
121 cacaatgaga gcctcatctc aagccaggcc tcgagctact tcattgacgc tgccacagtt
181 gacgacagtg gagagtacag gtgccagaca aacctctcca ccctcagtga cccggtgcag
241 ctagaagtcc atatcggctg gctgttgctc aggccccctc gtgggtgtt caaggaggaa
301 gaccctatcc acctgaggtg tcacagctgg aagaacactg ctctgcataa ggtcacatat
361 ttacagaatg gcaaaggcag gaagtatttt catcataatt ctgacttcta cattccaaaa
421 gccacactca agacagcgg ctcctacttc tgcaggggc ttgttgggag taaaaatgtg
481 tcttcagaga ctgtgaacat caccatcact caaggtttgt cagtgtcaac catctcatca
541 ttc
```

(human FcγRIIIB)                                    SEQ ID No. 9

```
MDLPKAVVFLE PQWYSVLEKD SVTLKCQGAY SPEDNSTQWF HNENLISSQA SSYFIDAATV
NDSGEYRCQT NLSTLSDPVQ LEVHIGWLLL QAPRWVFKEE DPIHLRCHSW KNTALHKVTY
LQNGKDRKYF HHNSDFHIPK ATLKDSGSYF CRGLVGSKNV SSETVNITIT QGLAVSTISS
F
```

(human FcγRIIIB, cDNA)                              SEQ ID No. 10

```
  1 atggatctcc caaaggctgt ggtgttcctg agcctcaat ggtacagcgt gcttgagaag
 61 gacagtgtga ctctgaagtg ccagggagcc tactcccctg aggacaattc cacacagtgg
121 tttcacaatg agaacctcat ctcaagccag gcctcgagct acttcattga cgctgccaca
181 gtcaacgaca gtggagagta caggtgccag acaaacctct ccaccctcag tgacccggtg
241 cagctagaag tccatatcgg ctggctgttg ctccaggccc ctcgtgggt gttcaaggag
301 gaagacccta ttcacctgag gtgtcacagc tggaagaaca ctgctctgca taaggtcaca
361 tatttacaga atggcaaaga caggaagtat tttcatcata attctgactt ccacattcca
421 aaagccacac tcaaagatag cggctcctac ttctgcaggg ggcttgttgg gagtaaaaat
481 gtgtcttcag agactgtgaa cattaccatc actcaaggtt tggcagtgtc aaccatctca
541 tcattc
```

-continued (SM101 variant)

SEQ ID No. 11

APPKAVLKL EPQWINVLQE DSVTLTCRGT HSPESDSIQW FHNGNLIPTH

TQPSYRFKAN NNDSGEYTCQ TGQTSLSDPV HLTVLSEWLV LQTPHLEFQE

GETIVLRCHS WKDKPLVKVT FFQNGKSKKF SRSDPNFSIP QANHSHSGDY

HCTGNIGYTL YSSKPVTITV QAPSSSP

In the amino acid sequence shown in SEQ ID No. 1 the M (methionine) residue at position 1 (i.e., at the start of the amino acid sequence) may lack. This variant amino acid sequence is disclosed herein as SEQ ID No. 11 and is a preferred amino acid sequence of the present invention.

(SM101 variant, cDNA)

SEQ ID No. 12

```
  1 GCACCGC CGAAAGCAGT TCTGAAACTG GAACCGCAGT GGATTAACGT TCTGCAGGAAGAT

61 AGCGTTA CCCTGACCTG TCGTGGCACC CATAGCCCGG AAAGCGATAG CATTCAGTGGTTT

121 CACAACG GCAATCTGAT TCCGACCCAT ACCCAGCCGA GCTATCGTTT TAAAGCGAACAAC

181 AACGATA GCGGCGAATA TACCTGTCAG ACCGGTCAGA CCAGCCTGAG CGATCCGGTTCAT

241 CTGACCG TTCTGAGCGA ATGGCTGGTT CTGCAGACCC CGCATCTGGA ATTTCAGGAAGGC

301 GAAACCA TTGTTCTGCG TTGCCACAGC TGGAAAGATA AACCGCTGGT TAAAGTTACCTTC

361 TTCCAGA ACGGCAAAAG CAAAAAATTC AGCCGTAGCG ATCCGAATTT TAGCATTCCGCAG

421 GCGAATC ATAGCCATAG CGGCGATTAT CATTGTACCG GCAACATTGG CTATACCCTGTAT

481 AGCAGCA AACCGGTGAC CATTACCGTT CAGGCGCCGA GCAGCAGCCC GTAA
```

The soluble Fc gamma receptor can be administered in any suitable form. However, in one preferred embodiment the receptor is administered intravenously.

It is further contemplated that the soluble Fc gamma receptor can be singularly, or it can be repeatedly administered.

The present invention further relates to a pharmaceutical composition comprising a soluble Fc gamma receptor for the treatment of autoimmune bullous diseases. Said pharmaceutical composition can further optionally comprise anti-inflammatory agents, immunosuppressive agents, and/or anti-CD20 antibody together with a pharmaceutically acceptable carrier or diluent.

In a further aspect, the present invention involves a kit comprising a soluble Fc gamma receptor the treatment of autoimmune bullous diseases. Said kit can further optionally comprise one or more of anti-inflammatory agents, immunosuppressive agents, and/or anti-CD20 antibody together with a pharmaceutically acceptable carrier or diluent.

In yet a further aspect, the present invention also relates to a method of treatment of autoimmune bullous diseases in a subject in need thereof that comprises a step of administering a therapeutically effective amount of a soluble Fc gamma receptor to said subject.

In another aspect, the present invention also relates to the use of a soluble Fc gamma receptor for the preparation of a pharmaceutical composition for the treatment of autoimmune bullous diseases in a subject.

In still another aspect, the present invention relates to the use of a soluble Fc gamma receptor for the treatment of autoimmune bullous diseases in a subject.

Also, the present invention relates to a method for the production of a pharmaceutical composition for the treatment of autoimmune bullous diseases in a subject, comprising admixing a soluble Fc gamma receptor with a pharmaceutically acceptable carrier, diluent or excipient.

(SM101) (p=0.031, t-test). C Representative clinical pictures 4 weeks after allocation to treatment in PBS (left upper panel) and sCD32 (SM101) (right upper panel) treated mice.

Figure 4:
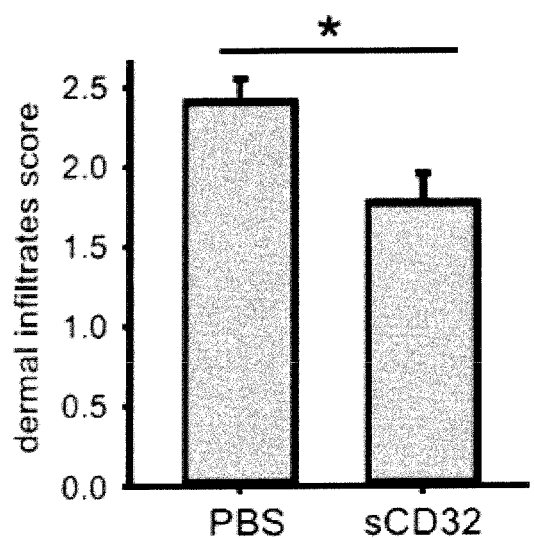
Figure 4:
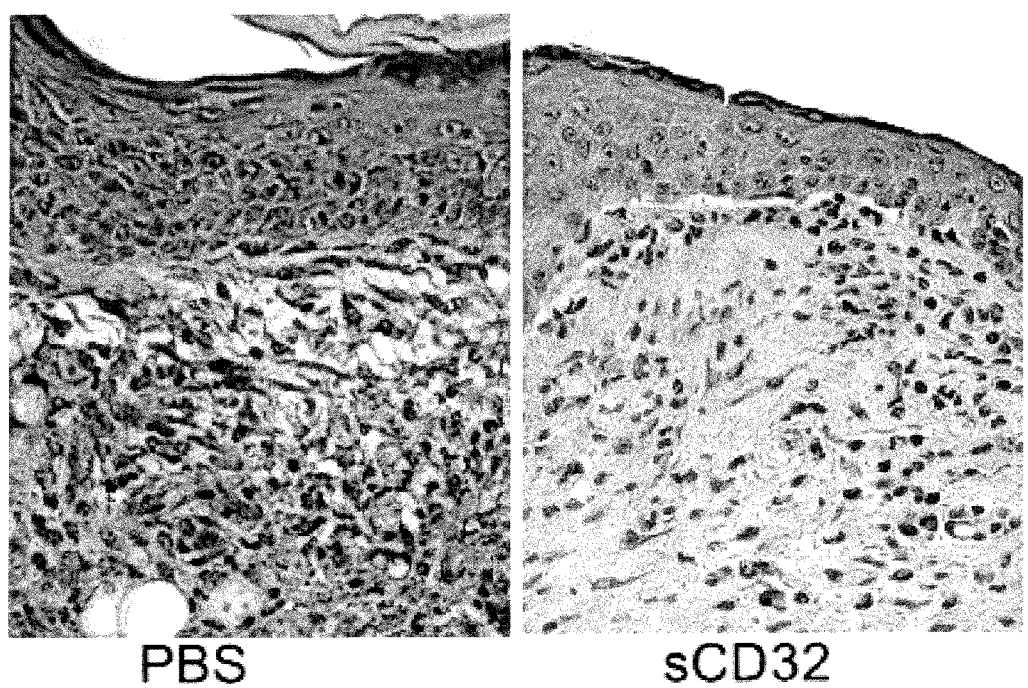

FIG. 4 A The score of dermal infiltrates is significantly lower in mice treated with sCD32 (SM101) (p<0.05, t-test). B Representative histology pictures show a reduced dermal inflammatory infiltrate in mice treated with sCD32 (SM101) (right) compared PBS (left).

Figure 5:
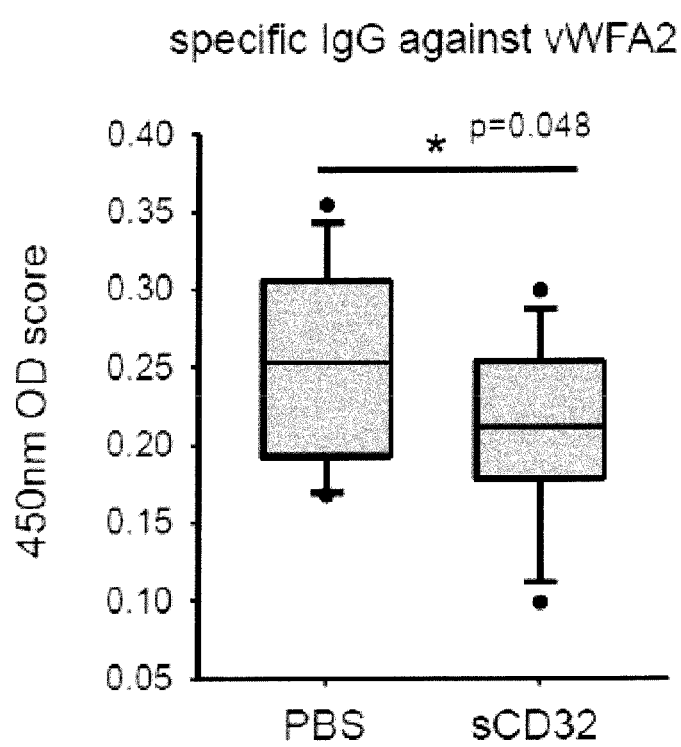

FIG. 5 Serum autoantibody against vWFA2 measured by ELISA at the end of the treatment period. Mice treated with sCD32 (SM101) had approximately 20% less antigen-specific autoantibodies compared to control mice (p=0.048; t-test).

FIG. 6A Relative fluorescence intensity level of tissue-deposit IgG measured by ImageJ at the end of the treatment period. All mice show IgG deposits at the DEJ by direct immunofluorescence (DIF). The fluorescence intensity was not different among the treatments. B Representative pictures of DIF IgG deposits at the end of the treatment period.

DETAILED DESCRIPTION

The present inventors have surprisingly observed that soluble Fc gamma RII receptor (sCD32=SM101), in particular and preferably, the sCD32 being SM101 as described herein, was able to inhibit the release of reactive oxygen species (ROS) from neutrophils activated by IgG immune complexes (IC) in vitro. Further, sCD32 could impair the dermal-epidermal separation on cryosections on human skin incubated with sera of Bullous pemphigoid patients in the presence of peripheral blood mononuclear cells (PBMCs). Strikingly, the promising therapeutic potential of sCD32 could be validated in mouse models of Epidermolysis bullosa acquisita (EBA): sCD32 significantly reduced clinical disease severity and, histologically, a significant decrease in the dermal leucocyte infiltration and an approximately 20% reduction in circulating antigen-specific autoantibodies compared to control. These promising results suggest that soluble Fc gamma receptors have a considerable potential for treatment of autoimmune bullous diseases.

Therefore, in a first aspect, the invention relates to the use of soluble Fc gamma receptor for use in a method of treatment of autoimmune bullous diseases.

The term "Fc gamma receptor" is used herein interchangeably with "FcgR" or "Fcγ receptor" or "FcγR" and comprises both membranous FcgRs and soluble FcgRs. Fc gamma receptors belong to the immunoglobulin superfamily of proteins and are found on many hematopoietic lineages. As their name indicates, Fc receptors recognize and bind to the Fc (fragment, crystallizable) part of antibodies, i.e. the fragment that corresponds to the two C-terminal domains of both heavy chains of the antibody and typically interacts with effector molecules and cells.

FcγRs recognize IgG antibodies. There are four IgG subclasses in humans, named in order of their abundance in the serum (IgG1, IgG2, IgG3, IgG4, with IgG1 being the most abundant IgG type). Three classes of FcγRs exist in humans: FcγRI (CD64), FcγRII (CD32) and FcγRIIIA (CD16). Furthermore, FcγRs occur in various isoforms, i.e. functionally similar Fc gamma receptors that have a similar but not an identical amino acid sequence. Said isoforms include FcγRlA, B1, B2, C; FcγRIIA1-2, B1-3, C and, further, several alleles (FcγRIIa1-HR, -LR; FcγRIIIb-NA1, -NA2) (van de Winkel and Capel, Immunol. Today 1993, 14:215-221). The different classes and isoforms of FcγR may differ with regard to their affinity to IgG and specifically to the different IgG subclasses. Typically, FcγR occur as type I transmembrane proteins or in soluble forms but there also exists a glycosylphosphatidylinositol anchored form of the FcγRIII (FcγRIIIB).

The present invention provides kits and compositions comprising soluble FcγRs and methods for treatment of AMDB. "Soluble FcγRs" are also referred to as "sFcγRs". In general, soluble forms of any FcγR class, isoform or allele can be identified by a preceding "s", e.g., sCD32 or sFcγRII refers to the soluble Fc gamma RII receptor. Preferred soluble Fc gamma receptors for the methods, kits and compositions according to the present invention are Fc gamma RIIA, Fc gamma RIIB, Fc gamma RIIIA or Fc gamma RIIIB. However, a soluble FcγRIIB receptors is especially preferred, in particular SM101 as described herein. Thus, in a more preferred embodiment, when referred herein to sCD32 or sFcγRII, SM101 is meant.

Typically, in contrast to membranous (i.e., membrane-bound) FcγR, soluble FcγR do not comprise a transmembrane region or an intracytoplasmatic tail.

Preferably, the soluble sFcγR of the invention is of human origin. The term "of human origin" is to be construed in its broadest sense. In general, it means that a sFcγR (or a region or fragment thereof) resembles or is similar to a human sFcγR (i.e., the protein found in the human body) in terms of amino acid sequence and/or structure. In general, soluble proteins and peptides can be obtained by extraction from human tissues or bodily fluids, e.g. from blood plasma by using blood plasma fractionation, a method that has been described in the prior art (Burnouf (2007)).

Alternatively, the soluble sFcγR "of human origin" can be a recombinant sFcγR that is obtained by expression of a recombinant nucleic acid in a host cell, e.g. as described by Sondermann and Jacob (1999). Briefly, a gene of interest is obtained from an organism and introduced into a vector, e.g. a plasmid or a virus, which is then used to transfer the gene into a host cell which expresses the recombinant gene and produces a recombinant protein product. Suitable host cells include, but are not limited to, prokaryotic cells (e.g., *E. coli, B. subtilis*) or eukaryotic cells such as yeast cells (e.g., *Saccharomyces, Pichia*), insect cells (e.g., Sf9, Hi5 cells), or mammalian cells (e.g., COS, CHO, BHK, HEK293, VERO, HeLa, MDCK, Wi38, Swiss 3T3, NIH 3T3, PER C6, SP2/0). The person skilled in the art will readily know which host cell to select in order to obtain a sFcγR that is suitable for the treatment of a particular AMDB and/or for the preparation of a pharmaceutical composition. For example, in some embodiments, an unglycosylated sFcγR may be desired. The person skilled in the art may then select a prokaryotic host cell for expression of the sFcγR that is devoid of the enzyme machinery necessary for protein glycosylation.

The term further encompasses sFcγRs that, in comparison to wild type sFcγR, have been modified or altered with regard to the amino acid sequence, and include, e.g., additional glycosylation sites or the like. However, also non-glycosylated forms of sFcγRs are envisaged and are a preferred embodiment of sFcγRs.

In a preferred embodiment, the soluble FcγR of the invention comprises or consists of an amino acid sequence corresponding to that of SEQ ID NO.: 1 (SM101, recombinant soluble human FcγRIIB), SEQ ID NO.: 3 (FcγRIIB), SEQ ID NO.: 5 (FcγRIIA), SEQ ID NO.: 7 (FcγRIIIA), SEQ ID NO.: 9 (FcγRIIIB), or SEQ ID NO.: 11 (SM101 variant). The invention also encompasses the use of soluble FcγRs that have at least 90%, preferably 95% identity to the proteins of SEQ ID Nos.: 1, 3, 5, 7, or 9. In order to determine the sequence identity a comparison is made by aligning the sequences in a manner to provide the maximum correspondence of amino acids. In a preferred embodiment, the soluble human receptor is SM101 (SEQ ID NO.:1 or SEQ ID NO.: 11, which is a soluble FcγRIIB receptor.

According to the present invention, sFcγR is used for treatment of autoimmune bullous diseases. "Autoimmune bullous diseases", abbreviated AMBD, sometimes also referred to as "autoimmune blistering diseases", "autoimmune bullous dermatoses" or "autoimmune blistering dermatoses" as used herein are acquired chronic diseases that are characterized by blistering of the skin and/or mucous membranes and are typically associated with an immune response to structural proteins that maintain cell-cell and/or cell-matrix adhesion. Several studies have suggested a pivotal role of FcγRs in autoimmune diseases. However, the present inventors were the first to recognize the potential of sFcγR for treatment of AMDB, and could show that their approach resulted in unexpected and promising effects both in an indirect-transfer setup with bullous pemphigoid (BP) patient's sera as well as in a mouse model of epidermolysis bullosa acquisita (EBA). Autoimmune bullous diseases can be classified into four major groups: The pemphigus diseases and pemphigoid diseases, epidermolysis bullosa acquisita and dermatitis herpetiformis. The pemphigus group comprises blistering diseases typically characterized by intraepidermal blister formation, the loss of cell-cell adhesion of keratinocytes and the deposition of autoantibodies in the intercellular junctions of keratinocytes.

The other diseases are typically characterized by sub-epidermal blistering caused by the loss of attachment of basal keratinocytes to the underlying basement membrane and are associated with deposition of immunoreactants in the dermal-epidermal junction. "Immunoreactants" are substances exhibiting immunoreactivity, such as antibodies or complement proteins. In particular, it is envisaged that Fc gamma receptor is used for treatment of a disease selected from the group of pemphigus vulgaris (PV), pemphigus foliaceus (PF), bullous pemphigoid (BP), mucous membrane pemphigoid (MMP), pemphigoid gestationis, mucous membrane pemphigoid, linear IgA disease, lichen planus pemphigoides, epidermolysis bullosa acquisita (EBA), dermatitis herpetiformis, and bullous systemic lupus erythematosus (BSLE).

Without wishing to be bound by a specific theory, it is hypothesized that AMDB are mediated by autoreactive antibodies mainly of the IgG type that recognize and bind to structural elements of the skin, including desmogleins, integrins, type VII collagens and BP proteins, thereby forming immune complexes (ICs). The Fc portions of the IgG antibodies bound in immune complexes may then be recognized by activating FcγRs expressed on the surface of immune effector cells, triggering inflammatory and destructive responses such as an oxidative burst, cytokine release and phagocytosis by macrophages, antibody-dependent cytotoxicity (ADCC) by natural killer cells, degranulation of mast cells and ROS release from neutrophils. It is contemplated that sFcγR might elicit its beneficial effects in part by hampering the binding of membrane-bound FcγR expressed on effector cells of the immune system to the ICs. Further, it may prevent binding of C1q and activation of the complement system.

The term "autoreactive antibody" is used herein interchangeably with the term "autoantibody" and describes an antibody directed against one or more of the host's own proteins.

AMDB are an object of ongoing research and some AMDB diseases are extremely rare. Therefore, more distinct AMDB diseases or variants of known AMDB diseases may be characterized in the future. Treatment of such diseases and variants is also envisaged.

The subject to be treated is preferably a mammal, and more preferably a human.

A variety of routes are applicable for administration of the sFcγR of the present invention, including, but not limited to, orally, topically, transdermally, subcutaneously, intravenously, intraperitoneally, intramuscularly or intraocularly. In one preferred embodiment, sFcγR is administered intravenously, transdermally, intradermally or subcutaneously. However, any other route may readily be chosen by the person skilled in the art if desired. For example, when the sFcγR of the present invention is preferably administered intradermally, it is preferably administered by injection, e.g., with a syringe or pen, close to, next to or in the vicinity of blisters or any other microscopically or macroscopically visible signs or symptoms of pemphigoid disease.

Systems for transdermal delivery are fabricated as multi-layered polymeric laminates in which a drug reservoir or a drug—polymer matrix is sandwiched between two polymeric layers: an outer impervious backing layer that prevents the loss of drug through the backing surface and an inner polymeric layer that functions as an adhesive and/or rate-controlling membrane. Transdermal drug delivery systems comprise different systems such as the reservoir systems, microreservoir systems, and the combination of reservoir and matrix-dispersion systems.

In the reservoir system, the drug reservoir is embedded between an impervious backing layer and a rate-controlling membrane. The drug releases only through the rate-controlling membrane, which can be microporous or non-porous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer can be applied. In the Matrix systems and Drug-in-adhesive system the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the Matrix-dispersion system the drug is dispersed homogeneously in a hydrophilic or lipophilic polymer matrix. This drug-containing polymer disk then is fixed onto an occlusive baseplate in a compartment fabricated from a drug-impermeable backing layer. Instead of applying the adhesive on the face of the drug reservoir, it is spread along the circumference to form a strip of adhesive rim. The drug delivery system is a combination of reservoir and matrix-dispersion systems. The drug reservoir is formed by first suspending the drug in an aqueous solution of water-soluble polymer and then dispersing the solution homogeneously in a lipophilic polymer to form thousands of unleachable, microscopic spheres of drug reservoirs. The thermodynamically unstable dispersion is stabilized quickly by immediately cross-linking the polymer in situ. Transdermal drug delivery technology represents one of the most rapidly advancing areas of novel drug delivery. This growth is catalyzed by developments in the field of polymer science. Polymers are used in transdermal delivery systems in various ways, including as matrix formers, rate-controlling membranes, pressure-sensitive adhesives (PSAs), backing layers or release liners.

Polymers used in transdermal delivery systems should have biocompatibility and chemical compatibility with the drug and other components of the system such as penetration enhancers and PSAs. They also should provide consistent, effective delivery of a drug throughout the product's intended shelf life or delivery period and have generally-recognized-as-safe status.

Rectal applications can be compounded in many forms. Liquid rectal medicine solutions are given by enema. Creams, lotions and ointments are applied externally or inserted internally using an applicator. Suppositories might be prepared by mixing medicine with a wax-like substance to form a semi-solid, bullet-shaped form that will melt after insertion into the rectum. Intraperitoneal injection or IP injection is the injection of a substance into the peritoneum (body cavity). A further form of administration of an inventive composition is the topic administration, for instance in form of an ointment or cream. Such an ointment or cream may additionally comprise conventional ingredients, like carriers or excipients as described herein. The sFcγR can also be used in sprays, for example for inhalation. The sFcγR may also be added to foods.

Administration of the sFcγR may be accomplished once, or may be required repeatedly, for example in intervals, e.g. every 12 hours, every 24 hours, every 36 hours, every 48 hours, every 60 hours or every 72 hours. In other embodiments, sFcγR can be administered every week or every month.

The soluble Fc gamma receptors used according to the invention may be chemically modified. Generally, all kind of modifications of the soluble Fc gamma receptor are comprised by the present invention as long as they do not abolish the therapeutic effect of the receptor. In the context with the present invention the term "therapeutic effect" in general refers to the desirable or beneficial impact of a treatment, e.g. amelioration or remission of the disease manifestations. The term "manifestation" of a disease is used herein to describe its perceptible expression, and includes both clinical manifestations, hereinafter defined as indications of the disease that may be detected during a physical examination and/or that are perceptible by the patient (i.e., symptoms), and pathological manifestations, meaning expressions of the disease on the cellular and molecular level.

The therapeutic effect of the uses and methods described herein is additionally detectable by all methods and approaches that are established for indicating a therapeutic effect in AMDB treatment. Methods for monitoring the therapeutic effect of the compound according to the present invention include, but are not limited to, the methods described by Mihai and Sitaru (2007), such as clinical examination of the patient for the presence, number and severity of skin lesions, histological examination of fresh blisters by H&E staining, direct and indirect immunofluorescence microscopy, and detection of autoreactive circulating antibodies using immunoassays, including immunofluorescence, immunoblotting, enzyme-linked immunosorbent assay (ELISA) and immunoprecipitation. For the detection of tissue-bound autoreactive antibodies, direct immunofluorescence microscopy can be applied, by taking a biopsy from perilesional or uninvolved skin and subsequent treatment with, e.g., fluorescence-labeled anti-IgG antibodies. Circulating autoreactive serum antibodies can be detected by indirect immunofluorescence microscopy performed on frozen sections of normal tissues, such as monkey esophagus, rodent or monkey bladder and human skin. The technique can be performed on salt-split skin that has previously been incubated in 1 M NaCl. Patient's serum is added to the tissue and secondary fluorescence-labeled antibodies are added to detect the autoreactive antibodies bound to antigens in the skin.

Additionally or alternatively it is also possible to evaluate the general appearance of the respective patient (e.g., fitness, well-being) which will also aid the skilled practitioner to evaluate whether a therapeutic effect has been elicited. The skilled person is aware of numerous other ways which are suitable to observe a therapeutic effect of the compounds of the present invention.

Possible chemical modifications of the sFcγR include acylation or acetylation of the amino-terminal end or amidation or esterification of the carboxy-terminal end or, alternatively, on both. The modifications may also affect the amino group in the side chain of lysine or the hydroxyl group of threonine. Other suitable modifications include, e.g., extension of an amino group with polypeptide chains of varying length (e.g., XTEN technology or PASylation®), N-glycosylation, O-glycosylation, and chemical conjugation of carbohydrates, such as hydroxyethyl starch (e.g., HESylation®) or polysialic acid (e.g., PolyXen® technology). Chemical modifications such as alkylation (e. g., methylation, propylation, butylation), arylation, and etherification may be possible and are also envisaged.

It is preferred that the mentioned modifications do not reduce or abolish the advantageous capabilities of the sFcγR as described herein, i.e. the chemically modified compounds of the invention should preferably have capabilities which are comparable to the capabilities of the compounds which were evaluated in the appended examples. Comparable as used herein means, The sFcγR can also be used as part of a pharmaceutical composition. Thus, a further embodiment of the invention is the use of the sFcγR for the manufacture of a pharmaceutical composition for treatment of AMDB. It is to be acknowledged that the embodiments described in the context of the use of a sFcγR according to the present invention are equally applicable to the uses of the pharmaceutical composition comprising said sFcγR, mutatis mutandis. The pharmaceutical composition may further comprise a pharmaceutically acceptable carrier or diluent. Processes known per se for producing medicaments are indicated in Forth, Henschler, Rummel (1996) Allgemeine und spezielle Pharmakologie und Toxikologie, Urban & Fischer.

Pharmaceutical compositions of the invention comprise a therapeutically effective amount of the sFcγR and can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration.

By "therapeutically effective amount" is meant an amount of the sFcγR that elicits a therapeutic effect as described herein. The exact amount dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. For example, the sFcγR, in particular the human sFcγRIIB may be administered in a dose of about 0.1 to about 100 mg/kg, e.g., 0.1, 0.2, 0.3, 0.4, 0.5, 0.6, 0.7, 0.8, 0.9, 1.0, 10, 20, 30, 40, 50, 60, 70, 80, 90, or 100 mg/kg. Other preferred doses are from about 0.1-50 mg/kg, 1-10 mg/kg, 1-20 mg/kg, 1-30 mg/kg, 1-40 mg/kg, 1-50 mg/kg, 1-60 mg/kg, 1-70 mg/kg, 1-80 mg/kg, 1-90 mg/kg, or 1-100 mg/kg. Further preferred doses are from about 10-100 mg/kg, 20-100 mg/kg, 30-100 mg/kg, 40-100 mg/kg-50-100 mg/kg.

The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans. Accordingly, the pharmaceutical composition may further comprise a pharmaceutically acceptable carrier or excipient.

Pharmaceutically acceptable carriers that are suitable for formulating the composition according the invention comprise those described below for the composition. Exemplary carriers include (biodegradable) liposomes; microspheres made of the biodegradable polymer poly(D,L-lactic-cogly-colic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopdyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable carriers and excipients are inter alia described in Remington's Pharmaceutical Sciences, 15$^{th}$ Ed., Mack Publishing Co., New Jersey (1991) and Bauer et al., Pharmazeutische Technologie, 5$^{th}$ Ed., Govi-Verlag Frankfurt (1997).

The pharmaceutical composition of the present invention may further comprise one or more additional agents. Preferably, said agents are therapeutically effective for treatment of AMDB and, more preferably, are selected from the group of anti-inflammatory agents, immunosuppressive agents and/or anti-CD20 antibodies. Preferably, the person skilled will select agents that are therapeutically effective for the treatment of the specific AMDB to be addressed. Therapeutic approaches for the treatment of various AMDB have been reviewed, e.g., by Han et al. (2009), Mutasim (2007), and Bickle and York (2002).

"Anti-inflammatory agents" inhibit or reduce inflammation, e.g., by inducing the production of anti-inflammatory mediators and/or inhibiting the production of pro-inflammatory mediators. Suitable anti-inflammatory agents for treatment of AMDB include glucocorticoids, e.g. prednisone or methylprednisolone, and antibiotics having an anti-inflammatory effect, such as dapsone and tetracycline, as well as niacinamide.

Immunosuppressive agents inhibit or prevent activity of the immune system, e.g., by reducing lymphocyte proliferation. Exemplary immunosuppressive agents suitable for treatment of AMDB include, e.g., azathioprine, mycophenolate mofetil (MMF), cyclophosphamide, methotrexate, and cyclosporine. The person skilled in the art will acknowledge that some immunosuppressive agents may also be classified as anti-inflammatory agents, and vice versa.

An exemplary anti-CD20 antibody that is suitable for AMDB treatment is rituximab.

It is also envisaged that the sFcγR is can be used as part of a kit. Accordingly, in a further aspect, the present invention also relates to a kit comprising a sFcγR for use in a method of treatment of autoimmune bullous diseases.

The kit may be a kit of two or more parts, and comprises sFcγR and optionally a pharmaceutically acceptable carrier, diluent or excipient. The components of the kit may be contained in a container or vials. It is to be noted that all embodiments described in the context of the sFcγR, the pharmaceutical composition comprising said sFcγR and the methods of treatment can also be applied to the kit of the invention, mutatis mutandis. Generally all carriers are suitable that are pharmaceutically acceptable and enable a release at the desired sit of action. The person skilled in the art knows which type of carrier is suitable depending on the chosen administration route. For example, carriers in the context with e.g. a rectal application are e.g. multi matrix systems using methacrylic acid copolymers. If e.g. the desired site of action is the colon and the sFcγR is applied orally the carrier has to be resistant to gastric acid in order to enable a release of the sFcgR in the colon.

The kit may further comprise one or more agents selected from the group of anti-inflammatory agents, immunosuppressive agents, and/or anti-CD20 antibody together with a pharmaceutically acceptable carrier or diluent. Suitable agents for use in the kit have been described herein. It is envisaged that the agents are applied simultaneously, or sequentially, or separately with respect to sFcγR administration. The present invention further encompasses the application of the agents via different administration routes. Therefore, suitable agents for use in the kit further comprise, e.g., topical glucocorticoid formulations for simultaneous, or sequential, or separate use with intravenously administered sFcγR.

Another aspect of the present invention is a method of treatment of AMDB in a subject in need thereof, comprising administering a therapeutically effective amount of a soluble Fc gamma receptor to said subject. The person skilled in the art will acknowledge that the embodiments described herein in the context the sFcγR, the pharmaceutical composition and the kit of the present invention are applicable to the method of treatment, mutatis mutandis. The step of administering the sFcγR may optionally further combined with one or more steps of AMDB treatment, said steps being selected from the group of IVIg injection, plasmapheresis, and extracorporeal phototherapy.

In another aspect, the present invention also relates to the use of a soluble Fc gamma receptor for the preparation of a pharmaceutical composition for the treatment of autoimmune bullous diseases in a subject. In still another aspect, the present invention relates to the use of a soluble Fc gamma receptor for the treatment of autoimmune bullous diseases in a subject. The person skilled in the art will acknowledge that the embodiments described herein in the context the sFcγR, the pharmaceutical composition and the kit of the present invention are applicable to these uses, mutatis mutandis.

Also, the present invention relates to a method for the production of a pharmaceutical composition for the treatment of autoimmune bullous diseases in a subject, comprising admixing a soluble Fc gamma receptor with a pharmaceutically acceptable carrier, diluent or excipient.

"IVIg" or "high dose intravenous immunoglobulin" is a blood product that contains the pooled polyvalent IgG extracted from the plasma of over one thousand blood donors and is administered intravenously. "Plasmapheresis" as used herein means withdrawing blood from the patient, filtering out the cellular components, and returning them to the patient. "Extracorporeal phototherapy" involves administering a photoactivating agent (e.g., methoxypsoralen) to a patient, collecting the patient's peripheral blood and exposing a portion of the peripheral lymphocytes to ultraviolet (UV-A) light. Subsequently, the blood is reinfused into the patient along with the treated lymphocytes. These methods have been reviewed i.a. by Mutasim (2007). The person skilled in the art will readily know that combination of any of these treatments with the envisaged administration of sFcγR has to be carefully assessed, e.g., regarding the time-point of application, in order to cause the desired therapeutic effects. The therapeutic effect can then be evaluated as described herein.

The exact dose of sFcγR will depend on the purpose of the treatment (e.g. remission maintenance vs. acute flare of disease), and will be ascertainable by one skilled in the art using known techniques. As is known in the art and described above, adjustments for route of administration, age, body weight, general health, sex, diet, time of administration, drug interaction and the severity of the condition may be necessary, and will be ascertainable with routine experimentation by those skilled in the art.

The term "treatment" in all its grammatical forms includes therapeutic or prophylactic treatment of AMDB. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of AMDB.

A better understanding of the present invention and of its advantages will be had from the following examples, offered for illustrative purposes only. The examples are not intended to limit the scope of the present invention in any way.

EXAMPLES

Example 1: Production of Recombinant Soluble CD32

Human sCD32 (SM101) was expressed and purified as described elsewhere (Sondermann and Jacob, 1999).

Example 2: Generation of EBA Mice

Example 2.1: Maintenance

SJL/J mice were obtained from The Jackson Laboratories (Bar Harbor, Me.). Animals were fed acidified drinking water and standard chow ad libitum, and held on a 12-h light-dark cycle at the animal facility of the University of Lubeck. Mice aged, 8-10 weeks were used for the experiments. All clinical examinations, biopsies and bleedings were performed under anesthesia with intraperitoneal administration of a mixture of ketamine (100 µg/g) and xylazine (15 µg/g). The experiments were approved by the Animal Care and Use Committee (Kiel, Germany) and performed by certified personnel.

Example 2.2: Immunization and Treatment with sCD32 of Mice

Immunization and evaluation were performed as previously described (Iwata et al, 2013). Briefly, mice were immunized at the hind footpad with 60 µg of recombinant murine vWFA2 domain of COL7 (Leineweber et al, 2011) emulsified in the nonionic block copolymer adjuvant Titer-Max (ALEXIS Biochemicals). Mice were evaluated every week for presence of skin lesions (i.e., erythema, blisters, erosions, alopecia and crusts). Disease severity was expressed as the percentage of the body surface area affected by skin lesions, and total disease severity during observation period was calculated as area under the curve (AUC) of the recorded disease severity during the observation period. The relative disease score was calculated as disease score at allocation treatment. Therapeutic treatment with sCD32 or PBS was started by intraperitoneal injection when 2% or more of the body surface area was affected by skin lesions. Mice were weekly treated with 200 µg of sCD32, control mice received PBS. Serum was collected every week. Serum, ear skin, tail skin samples were obtained at the final day after 4 weeks of treatment and prepared for examination by histopathology and immunofluorescence (IF) microscopy.

Figure 3:
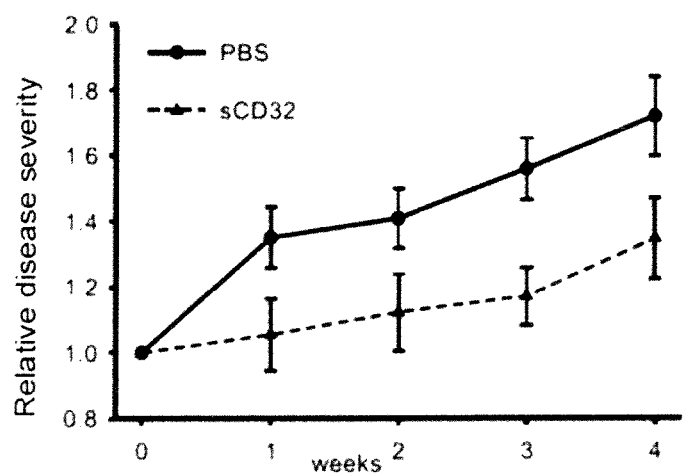
FIG. 3 A Experimental EBA was induced in SJL/J mice by immunization with vWFA2. After individual mice had 2% or more of their body-surface area affected by skin lesions, they were allocated to sCD32 (SM101) or PBS treatment. In the left panel, week 0 indicates starting point of treatment, and development of clinical disease severity in relation to the time of inclusion (week 0). Compared to PBS injected mice, sCD32 (SM101) treatment led to significantly lower clinical disease severity. Data is based on total 13 mice per group (*$p<0.05$, t-test), and expressed as mean±SEM. At allocation to treatment (week 0), average disease scores were not different (3.4±0.21% and 3.4±0.20% in PBS and sCD32 (SM101) treatment, respectively). B Overall disease severity (AUC) is shown that was lower in mice treated with sCD32
Figure 3:
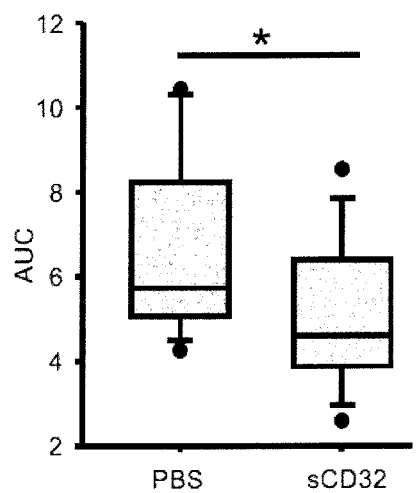
Figure 3:
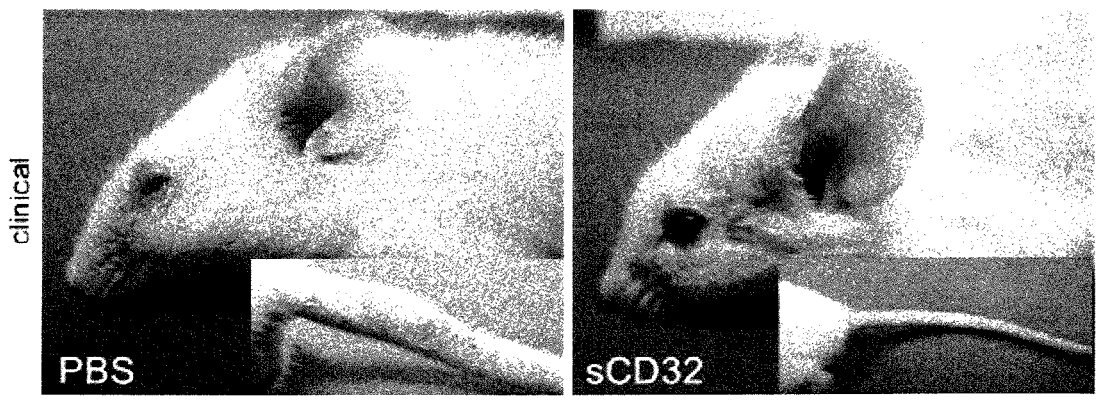

Compared to PBS injected mice, sCD32 treatment led to a significantly lower clinical disease severity (FIG. 3 A, left, $*p<0.05$, t-test). At inclusion to treatment (week 0), average disease scores were not different among the groups ($3.4\pm0.21\%$ and $3.4\pm0.20\%$) of affected body-surface area in PBS and sCD32 treatment, respectively). Cumulative disease severity expressed as AUC during the entire observation was also significantly lower in sCD32 treated mice as compared to PBS control mice (FIG. 3B, right, $p=0.031$, t-test). This degree of reduction is similar to the one observed in high dose corticosteroid (20 mg/kg i.p. daily) treatment (Hirose et al, 2013). At the end of the 4-week treatment period, PBS treated mice showed diffuse erythema and crusts on the ear and tail, and hair loss around eyes (FIG. 3C, left). In contrast, less erythema on the ear and no disease on tail or around eyes in mice treated with sCD32 were observed (FIG. 3C, right).

Example 3: Ex Vivo Assays

Example 3.1: ROS Production

Figure 1:
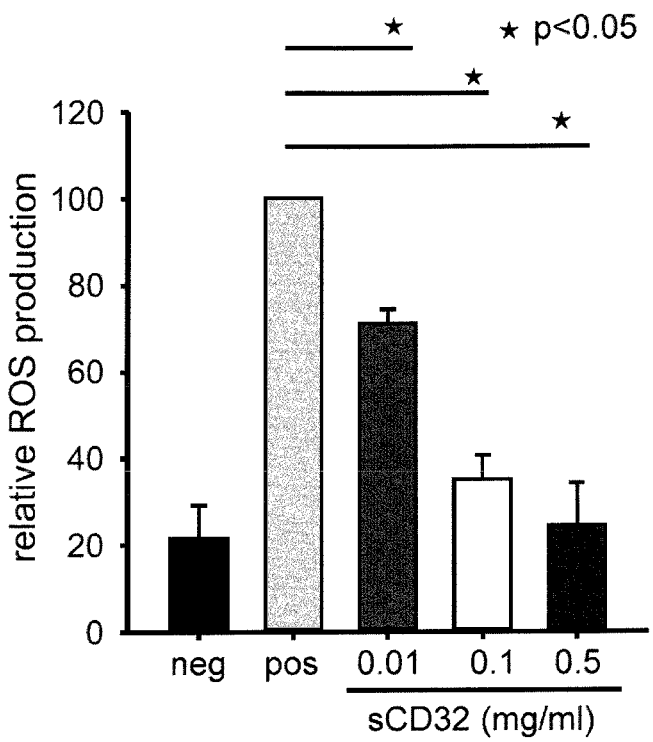
FIG. 1 IC were generated by incubation of human IgG on 96-well plates. After washing, human neutrophils were added in presence or absence of sCD32. Neutrophil activation was assayed by measuring ROS production. sCD32 (SM101) inhibited ROS production from IC-activated neutrophils in a dose-dependent manner. Data is based on 5 experiments per group (*$p<0.05$, ANOVA), and expressed as mean±SEM.

Reactive oxygen species (ROS) release capacities by autoantibodies of bullous pemphigoid were evaluated using an ex vivo assays as reported before (Yu et al, 2010). Briefly, to study ROS production, immune complexes (IC) were generated by incubation of 500 ng human IgG (50 µL×10 µg/mL) on 96-well plates (Maxisorb; Nunc, Roskilde, Denmark) at 4° C. over night. After washing plate, freshly isolated human neutrophils (50 µL×$10^7$ cells/mL) were added in the presence or absence of 0.01, 0.1 and 0.5 mg/mL of sCD32. Neutrophil activation was assayed to measure production of ROS by plate reader (VICTOR3, PerkinElmer, Santa Clara, Calif.).

sCD32 inhibited IC-induced neutrophil ROS production in a dose-dependent manner (FIG. 1). In detail, compared to positive control, 0.01, 0.1 and 0.5 mg/ml sCD32 significantly reduced ROS production by 30%, 65% or 75%, respectively.

Example 3.2: Dermal-Epidermal Separation

For this study serum samples from 21 bullous pemphigoid patients were used. All patients fulfilled the following inclusion criteria: (i) clinical picture of blistering disease of skin, (ii) binding of IgG autoantibodies to the epidermal side of blister in 1M NaCl-split normal human skin as shown by indirect immunofluorescence (IF) microscopy, (iii) reactivity to NC16A by ELISA. Sera from healthy volunteers served as negative controls. Prior to all procedures written informed consent was obtained from all patients and controls. The study was approved by the ethic committee of the University of Lübeck and was performed according to the Declaration of Helsinki.

Ex vivo autoantibody-induced, neutrophil-dependent dermal-epidermal separation was performed as described before (Sitaru et al, 2002). In brief, 6 µm thick cyosections from normal human skin were incubated with BP patients' serum at 37° C. for 1 hour. After washing with PBS, sections were incubated with $10^7$ cells/mL freshly isolated human leukocytes in the presence of or absence of 0.01, 0.1 and 0.5 mg/mL of sCD32 at 37° C. for 3 hours. Subsequently, sections were stained with H&E. Extent of dermal-epidermal separation, expressed as the percentage of epidermis separated from the dermis in each section was evaluated by an observer not aware of the treatment of the sections.

Figure 2:
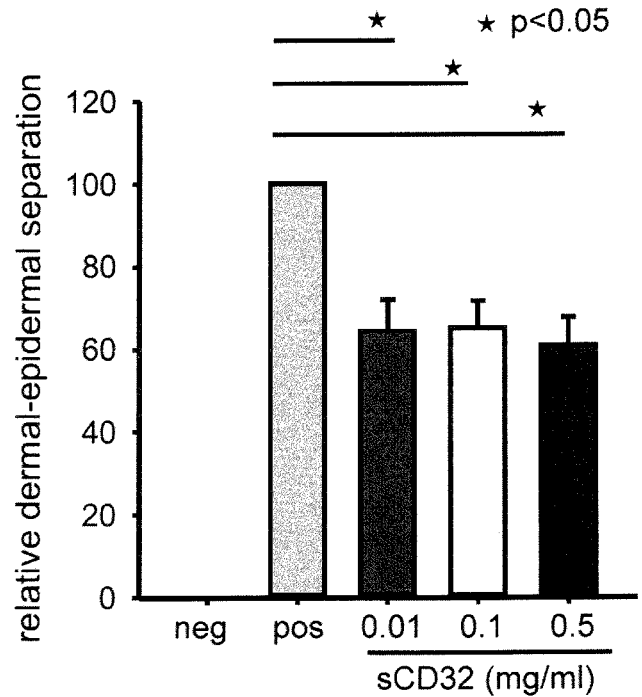
FIG. 2 Cryosections from normal human skin were incubated with sera from bullous pemphigoid patients. Subsequently leukocytes from healthy blood donors were added. This induced dermal-epidermal separation in the absence of sCD32 (SM101). In presence of sCD32 (SM101), autoantibody-induced, leukocyte-dependent dermal-epidermal separation was significantly impaired. Data is based on 21 experiments per group (*$p<0.05$, ANOVA), and expressed as mean±SEM.

The compound impaired FcγR-dependent (Yu et al, 2010), dermal-epidermal separation on cryosections of human skin incubated with sera of BP patients in the presence of PBMC (FIG. 2).

Example 4: Histological and IF Microscopy Studies

Samples of ear skin were fixed in 4% buffered formalin. 4 µm thick sections from paraffin-embedded tissues were stained with H&E. Histologically, relative dermal infiltrates were blindly quantified as 0 (no infiltrates), 1 (mild), 2 (intermediate) and 3 (severe). Tissue-bound antibodies were detected by direct IF microscopy on 6 µm frozen sections prepared from tissue biopsies using 100-fold diluted FITC-labeled antibodies specific to rabbit IgG (DakoCytomation) and murine C3 (Cappel Organon-Teknika). Fluorescence intensity at the DEJ was determined by ImageJ (http://rsbweb.nih.gov/ij/), using the dermal fluorescence for background subtraction.

Mice treated with sCD32 showed a significantly decrease in the dermal leukocyte infiltration, compared to PBS treated mice (p<0.05, FIGS. 4A and B).

Example 5: Measurement of Serum IgG and Anti-vWFA2 Antibodies

Figure 6:
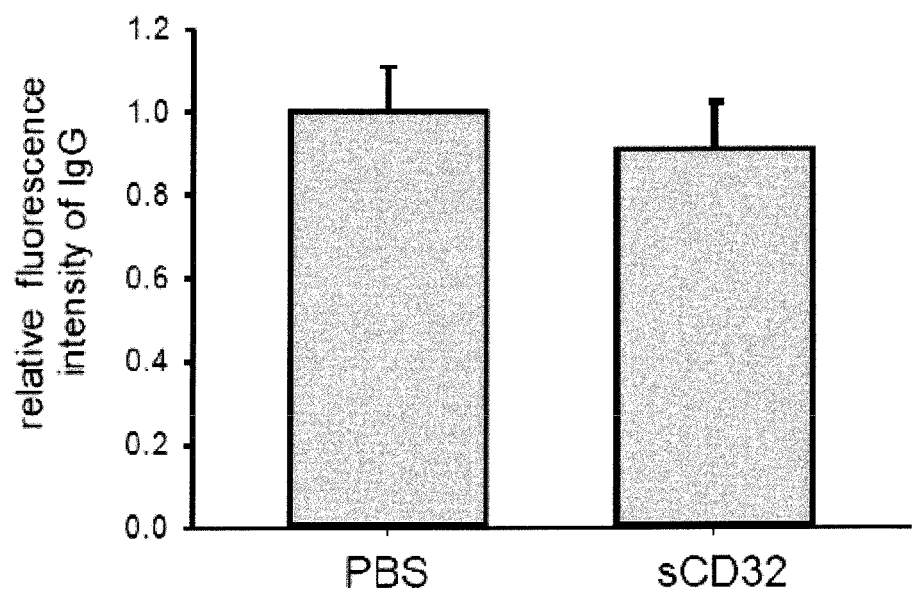
Figure 6:
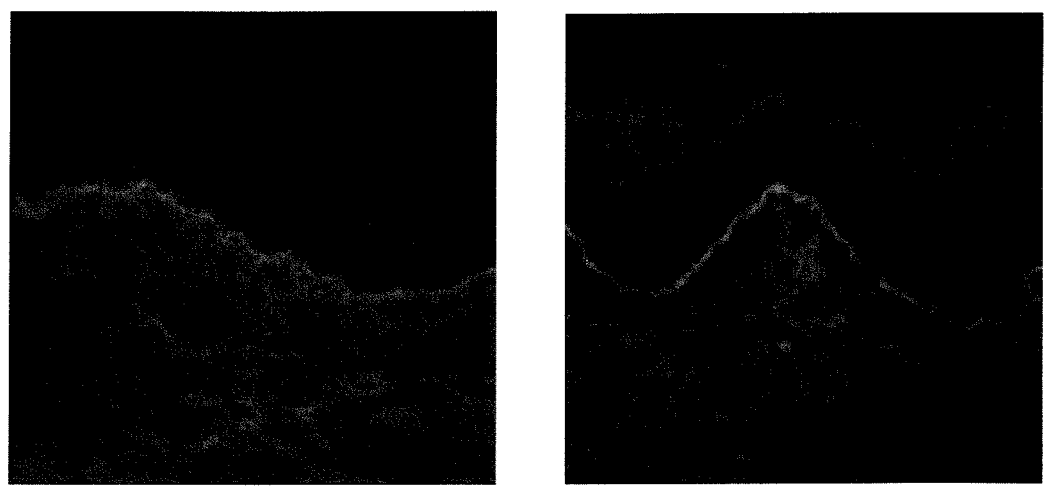

Serum anti-vWFA2 antibodies level was measured by ELISA as previously described (Iwata H et al, 2013). Total IgG was measure by mouse IgG ELISA quantization set (Bethyl Laboratories, Montgomery, Tex.) according to manufacturer's instruction.

sCD32 treatment also led to an approximately 20% reduction in circulating antigen-specific autoantibodies compared to PBS treated mice (FIG. 5, p=0.048; t-test), while total IgG were not significant different (data not shown). At the same time point, all mice showed similar IgG deposits at DEJ as determined by direct immunofluorescence (FIG. 6 A). Representative pictures of DIF show IgG deposits at DEJ (FIG. 6 B). This discrepancy between circulating and tissue bound autoantibodies may be due to the different half-live (Kasperkiewicz et al, 2010).

CITED LITERATURE

Bickle, K M, T R Roark and S Hsu. "Autoimmune Bullous Dermatoses: A review." *American Family Physician* 2002: 1861-1870.

Burnouf, T. "Modern plasma fractionation." *Transfusion Medicine Reviews* 2007: 101-117.

Collin, M und M Ehlers. "The carbohydrate switch between pathogenic and immunosuppressive antigen-specific antibodies." *Experimental Dermatology* 2013: 511-514.

Coca A, Sanz I B cell depletion in lupus and Sjögren's syndrome: an update. *Current Opinions in Rheumatology* 2009: 483-8.

Hauser S L et al. B-cell depletion with rituximab in relapsing-remitting multiple sclerosis. *The New England Journal of Medicine* 2008:676-88.

Hertl, M und D Zillikens. "Clinical and Molecular characterization of Autoimmune Bullous Diseases." *Journal of Investigative Dermatology* 2008: E19-21.

Kasperkiewicz et al., J. Pathol. (2012), Vol. 228, No. 1, 8-19

Konterman, R E. "Strategies for extended serum half-life of protein therapeutics." *Current Opinion in Biotechnology* 2011, 22 Aug.: 868-876.

Liu, Z und D S Rubinstein. "Pathophysiology of autoimmune bullous diseases." *The Journal of Investigative Dermatology* 2008: E22-24.

Ludwig, R. J., ISRN Dermatology Volume 2013

Magnusson, S E, M Andrén und K E Nilsson. "Amelioration of collagen-induced arthritis by human recombinant soluble Fc gamma RIIb." *Clinical Immunology* 2008: 225-233.

Mihai, S and C Sitaru. "Immunopathology and molecular diagnosis of autoimmune bullous diseases." *Journal of Cellular and Molecular Medicine* 2007: 462-481.

Mutasim, D F. "Therapy of autoimmune bullous diseases." *Therapeutics and Clinical Risk Management* 2007: 29-40.

Patel V L et al. Long-term outcome following B-cell depletion therapy with rituximab in children and adults with immune thrombocytopenia. *Blood* 2010:72.

Pescovitz M D et al. (2009) Rituximab, B-lymphocyte depletion, and preservation of beta-cell function. *The New England Journal of Medicine* 2009:2143-52.

Schmidt, E und R J Zillikens. "Pemphigoid diseases." *Lancet* 2013: 320-332.

Sitaru, C, S Mihai und D Zillikens. "The relevance of IgG subclass of autoantibodies for blister induction in autoimmune bullous skin diseases." *Archives of Dermatological Research* 2007: 1-8.

Sondermann, P und U Jacob. "Human Fcgamma receptor IIb expressed in *Escherichia coli* reveals IgG binding capability." *Biological Chemistry* 1999: 717-721.

Stone J H et al. Rituximab versus cyclophosphamide for ANCA-associated vasculitis. *The New England Journal of Medicine.* 2010: 221-32.

Takai, T. "Roles of Fc Receptors in Autoimmune diseases." *Nature Reviews Immunology* 2002: 580-592.

Weinblatt, M E, A Kavanaugh und M C Genovese. "An oral spleen tyrosine kinase (Syk) inhibitor for rheumatoid arthritis." *The New England Journal of Medicine* 2010: 1303-1312.

Werwitzke, S, D Trick und P Sondermann. "Treatment of lupus-prone NZB/NZW F1 mice with recombinant soluble Fc gamma receptor II (CD32)." *Annals of the Rheumatic Diseases* 2008: 154-161.

Yu et al. J. Inv. Dermatol. 2010, Vol. 130, No. 12, 2841-2844

The invention claimed is:

1. A method of treating an autoimmune bullous disease in a subject comprising administration of an effective amount of a soluble Fc gamma receptor, wherein the soluble Fc gamma receptor comprises an amino acid sequence selected from the group consisting of SEQ ID No: 1, SEQ ID No: 3, SEQ ID No: 5, SEQ ID No: 7, SEQ ID No: 9, and SEQ ID No: 11, wherein the soluble Fc gamma receptor is administered in a dose from 1-30 mg/kg, and wherein the autoimmune bullous disease is pemphigus vulgaris, pemphigus foliaceus, bullous pemphigoid, mucous membrane pemphigoid, pemphigoid gestationis, linear IgA disease, lichen planus pemphigoides, epidermolysis bullosa acquisita, or dermatitis herpetiformis.

2. The method of claim 1, wherein the soluble Fc gamma receptor is Fc gamma RIIB, Fc gamma RIIA, Fc gamma RIIIA, or Fc gamma RIIIB.

3. The method of claim 2, wherein the soluble Fc gamma receptor is Fc gamma RIIB.

4. The method of claim 3, wherein the soluble Fc gamma RIIB is of human origin.

5. The method claim 1, wherein the soluble Fc gamma receptor is of human origin.

6. The method of claim 1, wherein the soluble Fc gamma receptor comprises the amino acid sequence shown in SEQ ID No: 1 or SEQ ID No: 11.

7. The method of claim 1, wherein the subject is a mammal.

8. The method of claim 7, wherein the mammal is a human.

9. The method of claim 1, wherein the soluble Fc gamma receptor is administered intravenously or intradermally.

10. The method of claim 1, wherein the soluble Fc gamma receptor is administered at intervals selected from the group consisting of every 12 hours, every 24 hours, every 36 hours, every 48 hours, every 60 hours, and every 72 hours.

* * * * *